United States Patent
Ebinuma et al.

(10) Patent No.: US 11,566,074 B2
(45) Date of Patent: Jan. 31, 2023

(54) ANTIBODY FOR IMMUNOASSAY AND METHOD FOR PREPARING SAME

(71) Applicant: SEKISUI MEDICAL CO., LTD., Chuo-ku (JP)

(72) Inventors: Hiroyuki Ebinuma, Chuo-ku (JP); Kengo Fujimura, Chuo-ku (JP)

(73) Assignee: SEKISUI MEDICAL CO., LTD., Chuo-ku (JP)

(*) Notice: Subject to any disclaimer, the term of this patent is extended or adjusted under 35 U.S.C. 154(b) by 267 days.

(21) Appl. No.: 15/764,041

(22) PCT Filed: Sep. 29, 2016

(86) PCT No.: PCT/JP2016/078901
§ 371 (c)(1),
(2) Date: Mar. 28, 2018

(87) PCT Pub. No.: WO2017/057622
PCT Pub. Date: Apr. 6, 2017

(65) Prior Publication Data
US 2018/0273625 A1    Sep. 27, 2018

(30) Foreign Application Priority Data
Sep. 29, 2015 (JP) ............................. JP2015-191707

(51) Int. Cl.
| | | |
|---|---|---|
| *C07K 16/24* | (2006.01) | |
| *C07K 16/28* | (2006.01) | |
| *C12N 5/12* | (2006.01) | |
| *G01N 33/543* | (2006.01) | |
| *G01N 33/577* | (2006.01) | |
| *C07K 14/715* | (2006.01) | |
| *C12N 15/02* | (2006.01) | |
| *C12P 21/00* | (2006.01) | |
| *G01N 33/53* | (2006.01) | |
| *C07K 16/06* | (2006.01) | |
| *G01N 33/68* | (2006.01) | |

(52) U.S. Cl.
CPC ........ *C07K 16/2839* (2013.01); *C07K 14/715* (2013.01); *C07K 14/7155* (2013.01); *C07K 16/06* (2013.01); *C07K 16/065* (2013.01); *C07K 16/2866* (2013.01); *C12N 5/12* (2013.01); *C12N 15/02* (2013.01); *C12P 21/00* (2013.01); *G01N 33/53* (2013.01); *G01N 33/543* (2013.01); *G01N 33/577* (2013.01); *G01N 33/6869* (2013.01); *C07K 2317/73* (2013.01)

(58) Field of Classification Search
None
See application file for complete search history.

(56) References Cited

U.S. PATENT DOCUMENTS

| | | |
|---|---|---|
| 4,578,335 A | 3/1986 | Urdal et al. |
| 4,707,443 A | 11/1987 | Nelson et al. |

FOREIGN PATENT DOCUMENTS

| | | |
|---|---|---|
| EP | 1767942 A1 | 3/2007 |
| JP | 61-56083 A | 3/1986 |
| JP | 62-70761 A | 4/1987 |
| JP | 2-171199 A | 7/1990 |
| JP | 2014-186041 A | 10/2014 |
| WO | WO 99/43798 A1 | 9/1999 |
| WO | WO 2013/190029 A1 | 12/2013 |

OTHER PUBLICATIONS

International Search Report dated Dec. 13, 2016 in PCT/JP2016/078901 filed Sep. 29, 2016.
Jacques, Y. et al., "A soluble interleukin 2 receptor produced by a normal alloreactive human T cell clone binds interleukin 2 with low affinity", The Journal of Immunology, Oct. 1, 1987, vol. 139, No. 7, pp. 2308-2316.
Yang, Z.-Z. et al., "Soluble IL-2Rα facilitates IL-2-mediated immune responses and predicts reduced survival in follicular B-cell non-Hodgkin lymphoma", Blood, Sep. 8, 2011, vol. 118, No. 10, pp. 2809-2820.
Kimura, Y. et al., "Establishment and characterization of a monocytic cell line which expresses the interleukin-2 receptor", Japanese Journal of Cancer Research, Sep. 1986, vol. 77, pp. 862-865.
Extended European Search Report dated Mar. 18, 2019 in corresponding European Patent Application No. 16851793.6, 9 pages.
M. S. Loughnan, et al., "Soluble Interleukin 2 Receptors are Released from the Cell Surface of Normal Murine B Lymphocytes Stimulated with Interleukin 5", PNAS, vol. 85, XP55555432, May 1, 1988, pp. 3115-3119.
Mitsuo Honda, et al., "Fluorescence Sandwich Enzyme-Linked Immunosorbent Assay for Detecting Human Interleukin-2 Receptors", Journal of Immunological Methods, vol. 110, Issue 1, XP23794147, May 25, 1988, pp. 129-136.
Japanese Office Action dated Sep. 29, 2020 in Patent Application No. 2017-543587 (with English translation), 10 pages.

*Primary Examiner* — Michael D Pak
(74) *Attorney, Agent, or Firm* — Oblon, McClelland, Maier & Neustadt, L.L.P.

(57) ABSTRACT

Provided are a method of efficiently producing an sIL-2R antigen in an amount necessary for antibody generation, and a method of producing an anti-sIL-2R antibody using the antigen. Specifically, provided are a method of producing soluble interleukin-2 receptor, including culturing SCC-3 cells and recovering soluble interleukin-2 receptor from a culture of the cells, and a method of producing an anti-soluble interleukin-2 receptor antibody, including immunizing an animal with sIL-2R produced by the method.

4 Claims, 3 Drawing Sheets

[Fig. 1]
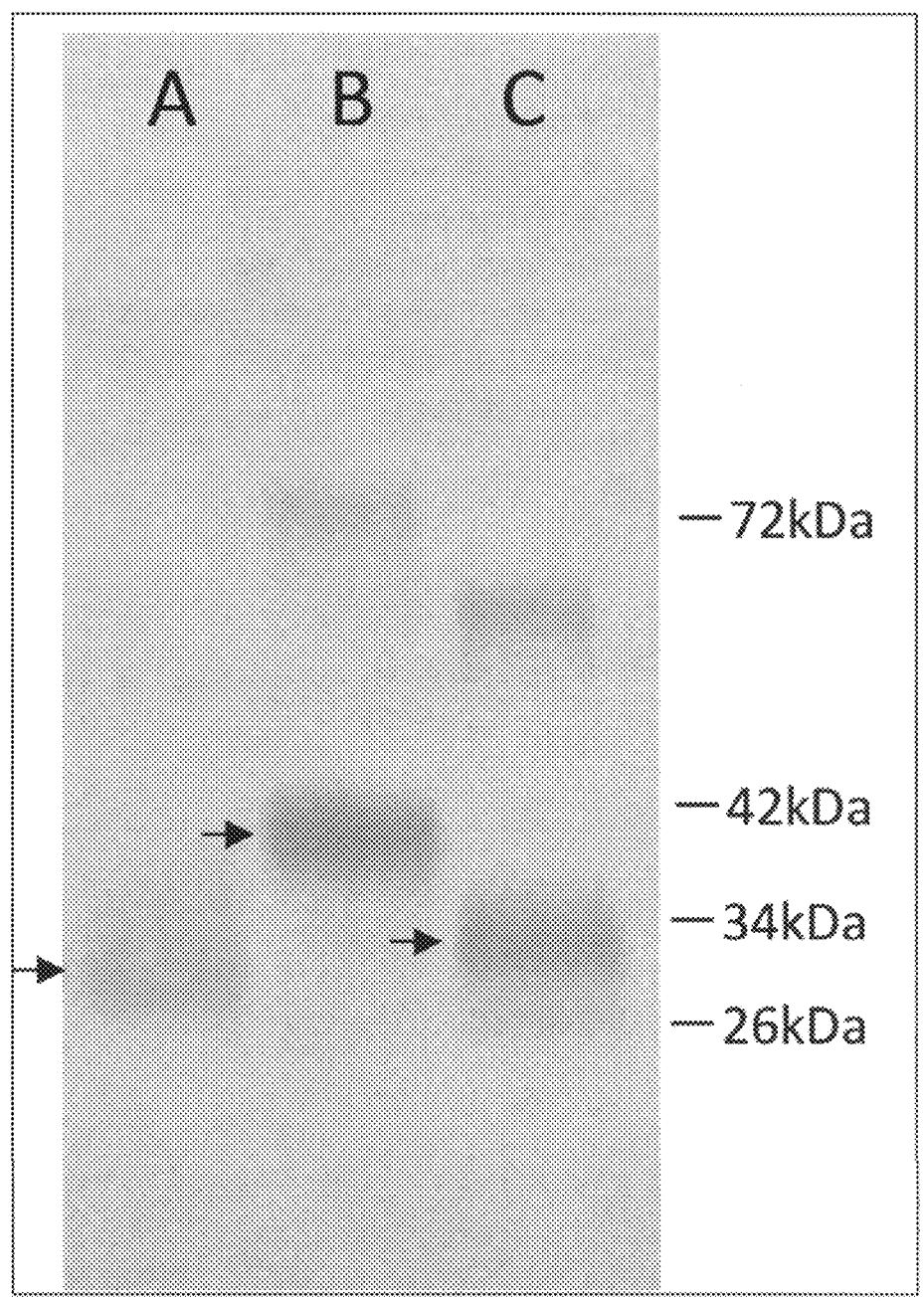

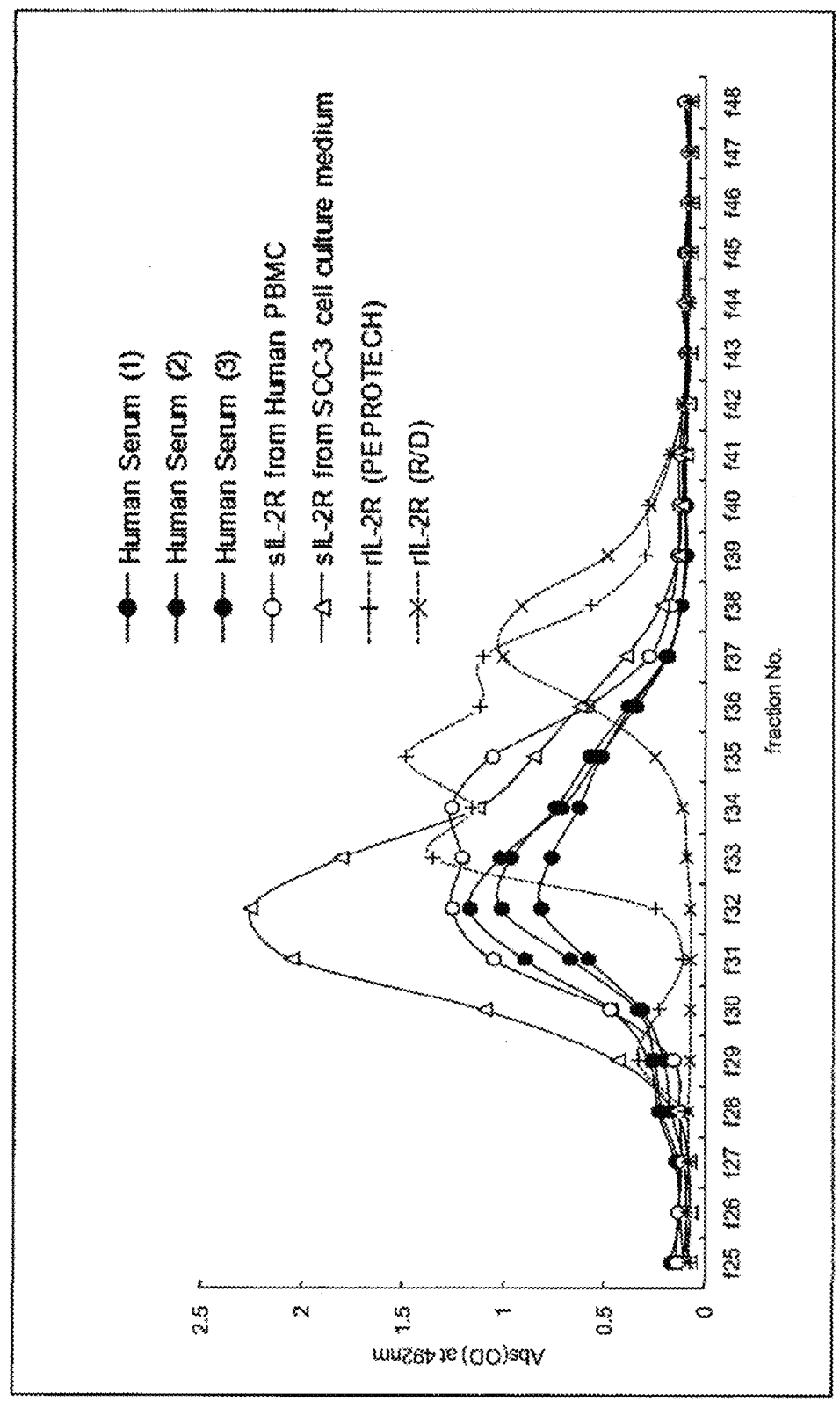
[Fig. 2]

[Fig. 3]
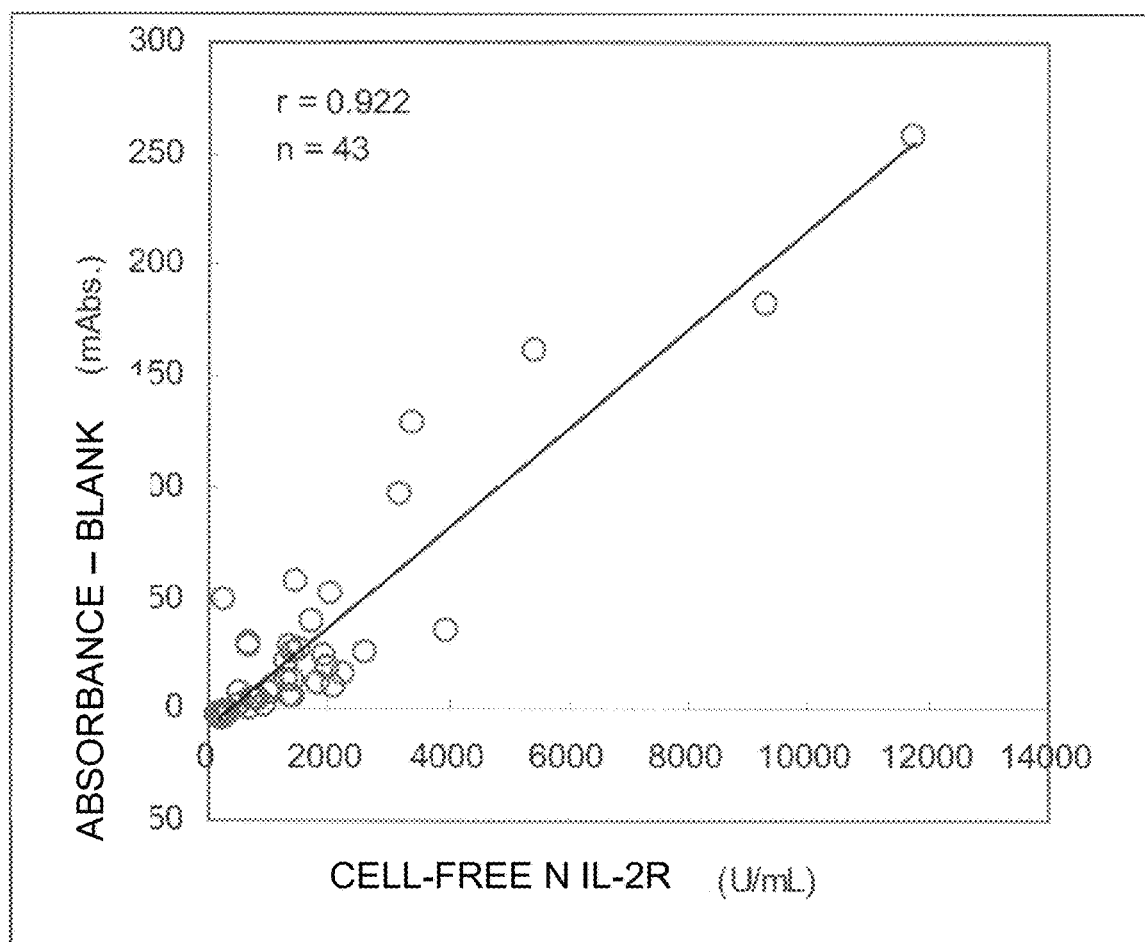

ANTIBODY FOR IMMUNOASSAY AND METHOD FOR PREPARING SAME

FIELD OF THE INVENTION

The present invention relates to an anti-soluble interleukin-2 receptor antibody, and a production method therefor.

BACKGROUND OF THE INVENTION

Soluble interleukin-2 receptor (hereinafter referred to as sIL-2R) is a soluble form of IL-2R generated by cleavage of an α chain of IL-2R, which is a cell membrane protein of T cells, and is present in blood of a living body. The sIL-2R is considered as an indicator reflecting immune activation of individuals because its ability to bind to IL-2 is retained and its blood concentration is elevated in patients with infections and various diseases involving activation of an immunoreaction. In clinical use, the sIL-2R has been utilized as a marker for diagnosis and follow-up of malignant lymphoma.

Hitherto, as a method of measuring the sIL-2R, a measurement reagent based on enzyme-linked immunosorbent assay (ELISA method) or chemiluminescent enzyme immunoassay (CLEIA method) using two kinds of monoclonal anti-sIL-2R antibodies against different epitopes has been developed and marketed as an in vitro diagnostic. However, the ELISA method has a problem in that the method involves complicated operations and the measurement requires a long period of time. Meanwhile, the CLEIA method has a drawback in that the method requires a dedicated measurement apparatus. Accordingly, there is a demand for development of a reagent for sIL-2R immunoassay that is simple, quick, and applicable to a general-purpose automatic analyzer.

Further, in order to measure the sIL-2R with higher precision, it is necessary to develop a reagent for sIL-2R immunoassay having higher specificity by controlling characteristics of an antibody, compatibility between the antibody and a solid support, and a non-specific reaction of the antibody. In order to improve development efficiency of the reagent for immunoassay, it is desired to acquire as wide a variety of options for anti-sIL-2R monoclonal antibodies serving as candidates as possible. To that end, it is required to use sIL-2Rs of various origins as immunogens to acquire required amounts of the sIL-2Rs as many as possible. In addition, the sIL-2R is also important as a standard for quantitative determination of measured sIL-2R. Accordingly, there is a need for a source capable of supplying the sIL-2R in a large amount and in a simple manner, which may be used as a source for an immunogen in anti-sIL-2R antibody generation or a source for a standard for sIL-2R quantitative analysis.

Regarding a related-art method of generating the anti-sIL-2R antibody, there is a report on a method involving stimulating peripheral blood mononuclear cells (PBMCs) collected from human blood with influenza virus and providing an antibody using the cells as an immunogen (Patent Literature 1). However, it is difficult to acquire human blood-derived PBMCs in a large amount, and hence it is not easy to obtain an immunogen in an amount necessary for reagent development by this method. As another method of generating the anti-sIL-2R antibody, there is a report on a method involving using, as an immunogen, IL-2R-expressing cells, such as a lymphoma cell line, as they are (Patent Literatures 2 and 3). However, this method involves extremely complicated operations involving observing expression of an antibody in a cell surface in advance, and besides, it is not guaranteed that an antibody obtained using the cells as an immunogen reacts with sIL-2R cleaved out of the cells. In addition, in Non Patent Literature 1, there is a description that the sIL-2R is secreted by some lymphoma cell lines. However, the sIL-2R is unsuitable as an immunogen for antibody generation because its concentration is extremely small. Meanwhile, in Non Patent Literature 2, it is reported that SCC-3, a monocytic non-Hodgkin's lymphoma cell line, expresses IL-2R on its cell surface, but there is no report on sIL-2R secretion by the cells.

As an antigen to be used for generating an antibody against a protein of interest, a recombinant protein of the protein of interest is also generally used. However, it is often experienced that a monoclonal antibody generated by immunization with a recombinant antigen provides no or weak reactivity with a native protein of interest contained in a specimen. This phenomenon is presumed to be, for example, due to the fact that the recombinant protein contains only a partial sequence of the native protein, or even when the recombinant protein contains a full-length sequence of the native protein, there is a change in three-dimensional structure based on a difference in protein folding. Further, even in the case where a plurality of kinds of antibodies capable of reacting with the native protein of interest can be generated by immunization with the recombinant protein, when the plurality of kinds of antibodies have antigenic determinants extremely similar to each other, the number of options for two kinds of monoclonal antibodies against different epitopes necessary for immunoassay extremely decreases.

CITATION LIST

Patent Literature

[Patent Literature 1] JP-A-62-70761
[Patent Literature 2] JP-A-61-56083
[Patent Literature 2] JP-A-02-171199

Non Patent Literature

[Non Patent Literature 1] Blood. 2011; 118, 2809-2820
[Non Patent Literature 2] Jpn. J. Cancer Res. 1986; 77, 862-865

SUMMARY OF THE INVENTION

Problem to be Solved by the Invention

The present invention relates to providing a method of efficiently producing an sIL-2R antigen in an amount necessary for antibody generation, a method of producing an anti-sIL-2R antibody using the antigen, and a reagent for sIL-2R immunoassay using the antibody.

Means for Solving the Problem

The inventors of the present invention found that a large amount of sIL-2R was secreted by SCC-3 cells, which were human monocytic cells derived from non-Hodgkin's lymphoma patients, and the shape of the sIL-2R secreted by the SCC-3 cells coincided with that of sIL-2R present in human blood and did not coincide with that of recombinant sIL-2R, and hence the cells were extremely suitable for producing sIL-2R to be utilized as an immunogen. The inventors of the present invention also found that a large number of options for combinations of two kinds of monoclonal antibodies for sIL-2R immunoassay were able to be acquired by antibody generation using, as an immunogen, the sIL-2R secreted by the SCC-3 cells.

That is, the present invention provides the following items [1] to [13].

[1] A method of producing soluble interleukin-2 receptor, comprising:
culturing SCC-3 cells; and
recovering soluble interleukin-2 receptor from a culture of the cells.

[2] A method of producing an anti-soluble interleukin-2 receptor antibody, comprising:
culturing SCC-3 cells to prepare soluble interleukin-2 receptor; and
immunizing an animal with the soluble interleukin-2 receptor. [3] The method according to the item [2], in which the antibody comprises a monoclonal antibody.

[4] The method according to the items [2] or [3], further comprising producing a hybridoma of spleen cells or lymph node-derived B cells collected from the immunized animal, and myeloma cells.

[5] The method according to any one of the items [2] to [4], in which the method is free of a step of stimulating the SCC-3 cells with influenza virus.

[6] A method of producing an anti-soluble interleukin-2 receptor antibody-producing hybridoma, comprising:
culturing SCC-3 cells to prepare soluble interleukin-2 receptor;
immunizing an animal with the soluble interleukin-2 receptor; and
subjecting spleen cells or lymph node-derived B cells collected from the immunized animal to cell fusion with myeloma cells.

An anti-soluble interleukin-2 receptor antibody-producing hybridoma, which is selected from the group consisting of 92212 (NITE BP-02124) and 92215R (NITE BP-02125).

[8] An anti-soluble interleukin-2 receptor antibody, which is obtained by immunizing an animal with soluble interleukin-2 receptor produced by SCC-3 cells.

[9] The antibody according to the item [8], in which the antibody comprises a monoclonal antibody.

[10] An immunoassay for human soluble interleukin-2 receptor, comprising using an anti-soluble interleukin-2 receptor antibody produced by the method of any one of the items [2] to [5].

[11] The immunoassay according to the item [10], in which the immunoassay comprises sandwich immunoassay using two kinds of monoclonal anti-soluble interleukin-2 receptor antibodies against different epitopes.

[12] The immunoassay according to the item [11], in which the sandwich immunoassay comprises latex turbidimetric immunoassay or sandwich ELISA.

[13] A reagent for measuring human soluble interleukin-2 receptor, comprising an anti-soluble interleukin-2 receptor antibody produced by the method of any one of the items [2] to [5].

[14] The reagent according to the item [13], in which the reagent comprises a reagent for performing latex turbidimetric immunoassay or sandwich ELISA.

Effects of Invention

According to the present invention, the sIL-2R antigen in an amount necessary for antibody generation can be efficiently provided. Thus, according to the present invention, the anti-s IL-2R antibody can be more efficiently produced, and hence a larger number of options for combinations of two kinds of monoclonal anti-sIL-2R antibodies suitable for sIL-2R immunoassay can be provided. Further, according to the present invention, the sIL-2R, which may be used as a substrate for specificity evaluation of the anti-s IL-2R antibody or a standard for quantitative analysis of the sIL-2R, can be provided in a large amount. Thus, the present invention enables efficient development of the reagent for sIL-2R immunoassay.

BRIEF DESCRIPTION OF THE DRAWINGS

FIG. 1 is an image for showing electrophoresis analysis results of SCC-3 cell-derived sIL-2R and recombinant sIL-2Rs (A: SCC-3 cell-derived sIL-2R, B and C: commercially available recombinant sIL-2Rs).

FIG. 2 is a graph for showing gel filtration chromatography analysis results of SCC-3 cell line-derived sIL-2R and recombinant sIL-2Rs.

FIG. 3 is a graph for showing a correlation between measurement results of the concentration of sIL-2R in a human serum specimen by an LTIA method using an antibody of the present invention and measurement results using a commercially available kit.

EMBODIMENTS FOR CARRYING OUT THE INVENTION

The present invention provides a method of producing sIL-2R from SCC-3 cells, and a method of producing an anti-sIL-2R antibody using, as an immunogen, sIL-2R obtained by the method.

The method of producing sIL-2R of the present invention comprises culturing SCC-3 cells and recovering soluble interleukin-2 receptor from a culture of the cells. Accordingly, the method of producing sIL-2R of the present invention is more specifically a method of producing human sIL-2R. The SCC-3 cells to be used in the method of the present invention are available from Japanese Collection of Research Bioresources (JCRB) Cell Bank (cell number: JCRB0115; see cellbank.nibio.go.jp/~cellbank/en/search_res_det.cgi?ID=285).

In the method of the present invention, the SCC-3 cells may be cultured in accordance with a general method in the art. Unlike in the case of human peripheral blood mononuclear cells (PBMCs), in the method of the present invention, it is not necessary that cells before culturing or during culturing be stimulated with influenza virus, concanavalin A (ConA), phytohemagglutinin (PHA), or the like so as to secrete sIL-2R. A medium for the culturing is preferably RPMI-1640 medium containing 10% FBS, which is recommended by the JCRB Cell Bank. Alternatively, FBS-free RPMI-1640 medium may be used for the purpose of eliminating the influence of FBS added into a medium in purifying sIL-2R secreted into a culture supernatant. The culturing is preferably performed under the conditions of 37° C. under 5% $CO_2$ for from 1 day to 7 days. A culture of the SCC-3 cells cultured by the above-mentioned procedure contains sIL-2R secreted by the cells. Accordingly, the sIL-2R may be recovered from the culture, for example, a culture medium or culture supernatant from which the cells have been removed. Alternatively, the sIL-2R may also be recovered from a lysate of the cells separated from the culture. Further, the sIL-2R may be recovered from both of the culture medium or culture supernatant and the cell lysate. A method of recovering the sIL-2R from the culture medium or culture supernatant is preferred because the method is simple and efficient.

The recovered sIL-2R may be used as it is as an immunogen, but is preferably purified. The purification only needs to be performed in accordance with protein purification means to be generally used in the art. Examples of the purification means include, but not limited to, ultrafiltration, electrophoresis, ion-exchange chromatography, hydrophobic chromatography, gel filtration, and affinity purification. Of those, affinity purification is preferred.

The method of producing sIL-2R of the present invention has high sIL-2R productivity, and hence allows the acquisition of a large amount of sIL-2R as compared to the related-art method involving producing sIL-2R by human PBMCs stimulated with influenza virus (e.g., Patent Literature 1). Accordingly, the method of producing sIL-2R of the present invention is extremely excellent means for providing sIL-2R to be used as an immunogen for anti-sIL-2R antibody generation, and is also extremely useful as means for providing a standard for sIL-2R quantitative analysis.

In the method of producing an anti-sIL-2R antibody of the present invention, the sIL-2R obtained from the SCC-3 cells by the above-mentioned procedure is used as an immunogen. In the method, the sIL-2R prepared by the above-mentioned procedure is used as an immunogen for immunizing an animal. In the method, purified sIL-2R, which is obtained by purifying the sIL-2R recovered from the culture of the SCC-3 cells by the above-mentioned procedure, is preferably used as an immunogen for immunizing an animal. Alternatively, in the method, unpurified sIL-2R recovered from the culture of the SCC-3 cells may be used as an immunogen for immunizing an animal. Alternatively, in the method, the culture of the SCC-3 cells, a culture medium or culture supernatant thereof, or the cells themselves separated from the culture may be used as an immunogen for immunizing an animal.

The method of producing an anti-sIL-2R antibody of the present invention is applicable to any of production of a polyclonal antibody and production of a monoclonal antibody. Each of the polyclonal antibody and the monoclonal antibody may be produced from an animal immunized with the immunogen in accordance with a method well known in the art.

For example, the polyclonal antibody is produced by immunizing an animal with the immunogen and then collecting antiserum from the animal. The polyclonal antibody may be produced by further purifying the antiserum as necessary. Examples of the animal to be immunized include, but not limited to, mice, rats, hamsters, rabbits, goats, sheep, and chickens.

The monoclonal antibody may be produced in accordance with a known monoclonal antibody generation method, for example, a method described in "Monoclonal Antibody", co-written by Hideaki Nagamune and Hiroshi Terada, Hirokawa Shoten (1990) or Jame W. Golding, "Monoclonal Antibody", 3rd edition, Academic Press, (1996). More specifically, the monoclonal antibody is produced by immunizing an animal with the immunogen and then generating hybridomas capable of producing a monoclonal antibody of interest from antibody-producing cells collected from the animal. Examples of the animal to be immunized include, but not limited to, mice and rats.

In each of the case of producing the polyclonal antibody and the case of producing the monoclonal antibody, the animal may be immunized in accordance with a general technique in the art. As an immunogen for the immunization, the above-mentioned culture of the SCC-3 cells, culture medium or culture supernatant thereof, cells separated from the culture, unpurified sIL-2R recovered from the culture, or purified sIL-2R, or a mixture of any two or more kinds thereof may be used as it is, or may be used in a liquid form by being suspended in a general buffer or physiological saline. The immunogen may be preferably in the form of a mixture with an adjuvant having an immunostimulating effect. An example of the adjuvant having an immunostimulating effect is complete or incomplete Freund's adjuvant. For example, the immunogen is preferably subcutaneously, intradermally, or intraperitoneally administered to the animal once or a plurality of times. The dose of the immunogen is appropriately determined depending on an administration route, an animal species, or the like, and a preferred dose thereof is from about 10 µg to about 1 mg per dose.

In the production of the monoclonal antibody, as the antibody-producing cells collected from the immunized animal to be used for hybridoma generation, spleen cells or lymph node-derived B cells isolated from the animal 3 days to 4 days after final immunization are suitable. In addition, myeloma cells (hereinafter referred to as "myeloma cells") to be subjected to cell fusion with the antibody-producing cells are preferably already established known various myeloma cell lines. Examples thereof include: NS1 (e.g., P3/NSI/I-Ag4-1) [Eur. J. Immunol. 6: 511-519 (1976)], SP2/O (e.g., SP2/O-Ag14) [Nature 276: 269 (1978)], P3-X63-Ag8.653 [J. Immunol. 123: 1548 (1979)], and P3-X63-Ag8U.1 [Curr. Top. Microbial. Immunol. 81: 1 (1978)] in mice; and Y3-Ag1.2.3. [Nature 277: 131-133 (1979)] and YB2/O (e.g., YB2/3HL/P2.G11.16Ag.20) [Methods Enzymol. 73B: 1 (1981)] in rats.

A generally used method, for example, a polyethylene glycol (PEG) method or a Sendai virus (hemagglutinating virus of Japan: HVJ) method may be used for the cell fusion between the antibody-producing cells and the myeloma cells in the hybridoma generation. A procedure for the cell fusion is the same as that in a general method. For example, in the case of the PEG method, PEG having an average molecular weight of from 1,000 to 6,000 is added dropwise at a concentration of from 30% to 60% to a mixed pellet of the myeloma cells and the antibody-producing cells (the number of the antibody-producing cells is from about 1 time to about 10 times as large as that of the myeloma cells), followed by mixing. A general selection medium, for example, a medium containing hypoxanthine, aminopterin, and thymidine (hereinafter referred to as "HAT") is used for selecting hybridomas capable of producing a monoclonal antibody of interest. Hybridomas obtained by culturing with the HAT medium may be used to perform screening and monocloning of hybridomas capable of producing an antibody of interest by a general limiting dilution method. The hybridomas capable of producing an antibody of interest are obtained, for example, by selecting hybridomas capable of producing an antibody capable of reacting with native sIL-2R by enzyme-linked immunosorbent assay (ELISA), RIA, or the like. Examples of the sIL-2R-producing hybridomas to be provided by the present invention include 92212 (NITE BP-02124) and 92215R (NITE BP-02125).

A monoclonal anti-sIL-2R antibody of interest may be produced by culturing the hybridomas capable of producing a monoclonal antibody of interest generated by the above-mentioned general procedure and then recovering the antibody in a culture supernatant. Alternatively, ascites containing the monoclonal anti-sIL-2R antibody may be recovered by administering the cultured hybridomas to a mammal having compatibility with the hybridomas.

In the method of producing an anti-sIL-2R antibody of the present invention, a monoclonal or polyclonal anti-sIL-2R antibody obtained by the above-mentioned procedure may be further isolated or purified as necessary. As means for isolating or purifying the antibody, there are given hitherto known methods, for example, salt precipitation, such as ammonium sulfate precipitation, gel filtration with Sephadex or the like, ion-exchange chromatography, and affinity purification with a protein A column or the like.

The anti-sIL-2R antibody obtained by the method of the present invention is preferably evaluated for its specificity for sIL-2R. A general method of investigating antibody specificity, for example, immunostaining (western blotting method), ELISA, or flow cytometry may be used for the specificity evaluation.

The anti-sIL-2R antibody obtained by the method of the present invention is suitably used as an antibody for sIL-2R immunoassay. Accordingly, the present invention also provides an sIL-2R immunoassay comprising using the anti-sIL-2R antibody obtained by the method of the present invention, and a reagent therefor. The reagent of the present invention is preferably a reagent for human sIL-2R immunoassay, more specifically a reagent for human blood sIL-2R immunoassay. In addition, the reagent is preferably a reagent for performing sIL-2R immunoassay based on, for example, immunostaining (western blotting method), ELISA, turbidimetric immunoassay (TIA), latex turbidimetric immunoassay (LTIA), enzyme immunoassay (EIA), chemiluminescence immunoassay (CLIA), or fluorescence immunoassay (FIA). The reagent is preferably a reagent for sIL-2R measurement based on sandwich immunoassay. For example, the reagent is a reagent for immunoassay based on sandwich ELISA using the anti-sIL-2R antibody obtained by the method of the present invention, and a substance having affinity with sIL-2R. In addition, for example, the reagent is a reagent for immunoassay based on LTIA or sandwich ELISA using two kinds of monoclonal anti-sIL-2R antibodies against different epitopes obtained by the method of the present invention.

The two kinds of monoclonal anti-sIL-2R antibodies against different epitopes suitable for LTIA or sandwich ELISA may be selected by constructing a sandwich ELISA measurement system using the two kinds of monoclonal anti-sIL-2R antibodies obtained by the method of the present invention as an immobilized antibody and a detection antibody, respectively, and evaluating detection sensitivity for sIL-2R in the system.

The reagent for sIL-2R immunoassay to be provided by the present invention contains an anti-sIL-2R antibody obtained by the method of the present invention, preferably two kinds of monoclonal anti-sIL-2R antibodies against different epitopes obtained by the method of the present invention. The reagent may further contain a solid support for binding the anti-sIL-2R antibody, a labeling or labeled antibody for detecting the anti-sIL-2R antibody, various buffers, or the like as necessary. In addition, the anti-sIL-2R antibody may be bound to the solid support as necessary.

The sIL-2R obtained by the method of producing sIL-2R of the present invention may also be used as a standard for sIL-2R quantitative analysis. As a method for the quantitative analysis, there is given quantitative analysis based on the above-mentioned immunostaining or immunoassay, such as ELISA, TIA, LTIA, EIA, CLIA, FIA, or sandwich immunoassay, using the anti-sIL-2R antibody, but the method is not limited thereto. More specifically, the concentration of the sIL-2R in a test sample is quantitatively determined by correcting a measured value of the test sample with reference to a measured value for a known concentration of an sIL-2R standard prepared from the sIL-2R obtained by the method of producing sIL-2R of the present invention.

Example

Now, the present invention is described in detail by way of Examples, but the present invention is not limited to Examples to be described below.

Comparative Example 1 Generation of Monoclonal Antibody Using Recombinant sIL-2R as Immunogen (1) Immunization of Animal Recombinant Human sIL-2 Receptor α (manufactured by Peprotech; Code: 200-02R) was dissolved in a 10 mM phosphate buffer (pH 7.2; hereinafter referred to as PBS) and mixed with an equal amount of Freund's complete adjuvant to prepare an emulsion. The emulsion was subcutaneously injected into female BALB/c mice and F344/Jcl rats every week five times in an amount of 50 µg/dose per animal. After that, an antibody titer in antiserum obtained by collecting blood from the tail vein of the mice and the rats was measured by an antigen-immobilized ELISA method to be described later.

(2) Measurement of Serum Antibody Titer

The Recombinant Human sIL-2 Receptor α used as the immunogen in the section (1) was dissolved at 0.5 µg/mL in PBS. 50 µL of the solution was dispensed into wells of a 96-well microplate, and the whole was left to standstill at room temperature for 1 hour. Next, the wells were washed three times with 300 µL of PBS containing 0.05% Tween (trademark) 20 (hereinafter referred to as PBST), and then blocked at room temperature for 1 hour by adding 200 µL of PBST containing 1% bovine serum albumin (hereinafter referred to as BSA-PBST). Further, the wells were washed three times with PBST, 50 µL of mouse antiserum diluted with BSA-PBST by a factor of from several hundreds to several tens of thousands was then added, and the whole was left to stand still at room temperature for 1 hour, followed by washing three times with PBST. After that, for a mouse antiserum sample, 50 µL of 7,500-fold diluted Anti mouse IgG (H+L) Goat IgG HRP (manufactured by Southern Biotech) was dispensed into the wells, and the whole was left to stand still at room temperature for 1 hour. For a rat antiserum sample, a polyclonal antibody generated (generated in our company) by immunizing rabbits with the Recombinant Human sIL-2 Receptor α was labeled with biotin and diluted with BSA-PBST to prepare a dilution liquid (2.0 µg/mL in terms of IgG content). 50 µL of the dilution liquid was dispensed into the wells, and the whole was left to stand still at room temperature for 1 hour. The wells were washed three times with PBST, 50 µL of a BSA-PBST solution (0.2 µg/mL) of HRP-labeled streptavidin (manufactured by PIERCE) was then added, and the whole was left to stand still at room temperature for 30 minutes.

Next, the wells were washed three times with PBST, 50 µL of a citrate buffer (pH 5.0) containing 0.2% orthophenylenediamine (OPD) and 0.02% hydrogen peroxide was then added, and the whole was left to stand at room temperature for 10 minutes. After that, 50 µL of 7.7% sulfuric acid was added to stop the enzyme reaction. An absorbance at a wavelength of 492 nm was measured, and an antibody titer was evaluated. The spleen or the lymph node was excised from the mice and rats that produced antisera having sufficiently elevated antibody titers, to thereby prepare spleen cells or lymph node-derived cells, which were used for hybridoma generation.

(3) Hybridoma Generation

Any one of the spleen cells and lymph node-derived cells prepared in the section (2), and myeloma cells were mixed with each other at a ratio of 6:1 in terms of the number of cells, and subjected to cell fusion by an ordinary method using polyethylene glycol. The myeloma cells used were SP2/O. The resultant fused cells were suspended at $2.5 \times 10^6$ cells/mL in terms of spleen cells in RPMI 1640 medium containing hypoxanthine, aminopterin, and thymidine (HAT), and 15% fetal calf serum. 200 μL of the suspension was dispensed into wells of a 96-well microplate and cultured in a $CO_2$ incubator at 37° C. under 5% $CO_2$ for 7 days. Thus, fused cells (hybridomas) were obtained.

(4) Production of Anti-sIL-2R Antibody-Producing Hybridoma (i) Selection of Mouse-Derived Hybridoma AffiniPure Goat Anti-mouse IgG (Jackson ImmunoResearch Laboratories, Code: 115-005-071) was dissolved at 10 μg/mL in PBS. 50 μL of the solution was dispensed into wells of a 96-well microplate, and the whole was left to stand still at room temperature for 1 hour. The wells were washed three times with 300 μL of PBST, and then blocked at room temperature for 1 hour by adding 200 μL of BSA-PBST. Next, the wells were washed three times with PBST, 50 μL of the culture supernatant of the mouse cell-derived hybridomas diluted two-fold was then added, and the whole was left to stand still at room temperature for 1 hour. The Recombinant Human sIL-2 Receptor α serving as an immunogen was diluted with BSA-PBST to prepare a dilution liquid (250 ng/mL). The wells were washed three times with PBST, 50 μL of the antigen dilution liquid was then added, the whole was left to stand still at room temperature for 1 hour, and the wells were washed three times with PBST. An anti-sIL-2R rabbit polyclonal antibody generated by immunizing rabbits with the Recombinant Human sIL-2 Receptor α was purified and labeled with biotin to prepare a labeled polyclonal antibody, followed by dilution (2 μg/mL) with BSA-PBST. 50 μL of the antibody dilution liquid was added to the wells, and the whole was left to stand still at room temperature for 1 hour. Next, the wells were washed three times with PBST, 50 μL of a BSA-PBST solution (0.2 μg/mL) of HRP-labeled streptavidin (manufactured by PIERCE) was then added, and the whole was left to stand still at room temperature for 30 minutes. The wells were washed three times with PBST, 50 μL of a citrate buffer (pH 3.7) containing 0.3 mg/mL tetramethylbenzidine (TMB) and 0.02% hydrogen peroxide was then added, and the whole was left to stand at room temperature for 10 minutes. After that, 50 μL of 7.7% sulfuric acid was added to stop the enzyme reaction. An absorbance at a wavelength of 450 nm was measured to select wells in which anti-sIL-2R antibody-producing hybridomas were present (positive wells).

(ii) Selection of Rat-Derived Hybridoma

AffiniPure Goat Anti-rat IgG (Jackson ImmunoResearch Laboratories, Code: 112-005-008) was dissolved at 10 μg/mL in PBS. 50 μL of the solution was dispensed into wells of a 96-well microplate, and the whole was left to stand still at room temperature for 1 hour. The wells were washed three times with 300 μL of PBST, and then blocked at room temperature for 1 hour by adding 200 μL of BSA-PBST. Next, the wells were washed three times with PBST, 50 μL of the culture supernatant of the rat cell-derived hybridomas diluted two-fold was then added, and the whole was left to stand still at room temperature for 1 hour. The Recombinant Human sIL-2 Receptor α serving as an immunogen was diluted with BSA-PBST to prepare a dilution liquid (250 ng/mL). The wells were washed three times with PBST, 50 μL of the antigen dilution liquid was then added, the whole was left to stand still at room temperature for 1 hour, and the wells were washed three times with PBST. Biotylated Anti-human IL-2Rα Goat Antibody (manufactured by R&D systems, Code: BAF223) was diluted (250 ng/mL) with BSA-PBST. 50 μL of the antibody dilution liquid was added to the wells, and the whole was left to stand still at room temperature for 1 hour. Next, the wells were washed three times with PBST, 50 μL of a BSA-PBST solution (0.2 μg/mL) of HRP-labeled streptavidin (manufactured by PIERCE) was then added, and the whole was left to standstill at room temperature for 30 minutes. The wells were washed three times with PBST, 50 μL of a citrate buffer (pH 3.7) containing 0.3 mg/mL tetramethylbenzidine (TMB) and 0.02% hydrogen peroxide was then added, and the whole was left to stand at room temperature for 10 minutes. After that, 50 μL of 7.7% sulfuric acid was added to stop the enzyme reaction. An absorbance at a wavelength of 450 nm was measured to select wells in which anti-sIL-2R antibody-producing hybridomas were present (positive wells).

(iii) Selection of Hybridoma Capable of Reacting with Native sIL-2R

Hybridomas capable of reacting with native sIL-2R were selected from the anti-sIL-2R antibody-producing hybridomas selected in the sections (i) and (ii). The selection was performed by the same procedure as in the section (i) or (ii). In this case, the same hybridoma culture supernatant as that contained in the positive wells was used as a hybridoma culture supernatant, and a culture supernatant of human PBMCs (secreting sIL-2R) stimulated with concanavalin A was used as an immunogen in place of the Recombinant Human sIL-2 Receptor α.

(iv) Establishment of Hybridoma

From the anti-sIL-2R antibody-producing hybridomas obtained in the section (iii), monocloning of the hybridomas was performed by a limiting dilution method. A total of 11 kinds of hybridomas including 3 kinds of mouse-derived hybridomas (clone numbers; 92201, 92202, and 92203) and 8 kinds of rat-derived hybridomas (clone numbers; 92204R, 92205R, 92206R, 92207R, 92208R, 92209R, 92210R, and 92211R) were obtained. 92204R out of the hybridomas was deposited by the applicant on Sep. 25, 2015 to NITE Patent Microorganisms Depositary (2-5-8 Kazusakamatari, Kisarazu, Chiba 292-0818, Japan). 92204 R: Receipt number: NITE BP-02123

(5) Evaluation of Antibody Combination Applicable to Sandwich Immunoassay

A monoclonal anti-sIL-2R antibody was purified from each of the 11 kinds of hybridomas generated in the section (4), and a combination of antibodies enabling a sandwich ELISA system was evaluated by a method described below. Each monoclonal anti-sIL-2R antibody was dissolved in PBS (10 μg/mL). 50 μL of the solution was dispensed into wells of a 96-well microplate, and the whole was left to stand still at room temperature for 1 hour. The wells were washed three times with 300 μL of PBST, and then blocked at room temperature for 1 hour by adding 200 μL of BSA-PBST. Next, the wells were washed three times with PBST, 50 μL of human PBMC-derived native sIL-2R (2,000 U/mL) was then added, and the whole was left to standstill at room temperature for 1 hour. Each monoclonal anti-sIL-2R antibody labeled with biotin was diluted with BSA-PBST to prepare a dilution liquid (0.4 μg/mL). The wells were washed three times with PBST, 50 μL of the antibody dilution liquid was then added, and the whole was left to stand still at room temperature for 1 hour. The wells were washed three times with PBST, 50 μL of a BSA-PBST solution of HRP-labeled streptavidin (manufactured by PIERCE) (0.2 μg/mL) was then added, and the whole was left to stand still at room temperature for 30 minutes. The wells were washed three times with PBST, 50 μL of a citrate buffer (pH 3.7) containing 0.3 mg/mL tetramethylbenzidine (TMB) and 0.02% hydrogen peroxide was then added, and the whole was left to stand at room temperature for 10 minutes. After that, 50 μL of 7.7% sulfuric acid was added to stop the enzyme reaction, and an absorbance at a wavelength of 450 nm was measured.

The evaluation results of combinations of the 11 kinds of monoclonal antibodies are shown in Table 1. In Table 1, absorbances at a wavelength of 450 nm of the combinations were assessed as follows: less than 0.5 OD: −; 0.5 OD or more: ++; and 1.0 OD or more: +++. The combination of antibodies achieving an absorbance change at a level enabling the sandwich ELISA system was only one combination of 92204R and 92205R.

TABLE 1

|  |  | Immobilized antibody | | | | | | | | | | |
|---|---|---|---|---|---|---|---|---|---|---|---|
|  |  | 92201 | 92202 | 92203 | 92204R | 92205R | 92206R | 92207R | 92208R | 92209R | 92210R | 92211R |
| Biotin- | 92201 | | − | − | − | − | − | − | − | − | − | − |
| labeled | 92202 | − | | − | − | − | − | − | − | − | − | − |
| antibody | 92203 | − | − | | − | − | − | − | − | − | − | − |
|  | 92204R | − | − | − | | +++ | − | − | − | − | − | − |
|  | 92205R | − | − | − | +++ | | − | − | − | − | − | − |
|  | 92206R | − | − | − | − | − | | − | − | − | − | − |
|  | 92207R | − | − | − | − | − | − | | − | − | − | − |
|  | 92208R | − | − | − | − | − | − | − | | − | − | − |
|  | 92209R | − | − | − | − | − | − | − | − | | − | − |
|  | 92210R | − | − | − | − | − | − | − | − | − | | − |
|  | 92211R | − | − | − | − | − | − | − | − | − | − | |

Example 1 Preparation of sIL-2R from SCC-3 Cell Line

An SCC-3 cell line (cell number: JCRB0115) distributed from Japanese Collection of Research Bioresources (JCRB) Cell Bank was initiated with a specified medium (RPMI-1640 containing 10% fetal bovine serum (FBS) and penicillin/streptomycin), and the cells were then sufficiently grown. The grown SCC-3 cells were harvested by centrifugation, washed with FBS-free RPMI-1640, then diluted with the same medium so as to have a cell concentration of $1 \times 10^6$ cells/mL, and cultured in a $CO_2$ incubator at 37° C. for 7 days.

After that, the cells were removed by centrifugation to recover a culture supernatant. The concentration of sIL-2R in the culture supernatant was measured with a commercially available kit (CELL-FREE N IL-2R; manufactured by Kyowa Medex Co., Ltd.). As a result, the concentration was as high as 18,000 U/mL. Thus, it was found that the sIL-2R was able to be easily acquired in an amount sufficient for preparation of an immunogen or a standard.

Comparative Example 2 Preparation of sIL-2R from Human PBMC Cells

PBMCs were recovered from human blood and stimulated with concanavalin A so as to secrete sIL-2R. The secreted sIL-2R was recovered and measured for its concentration by the same procedure as in Example 1. The concentration of the recovered sIL-2R was measured by the same procedure as in Example 1 (CELL-FREE N IL-2R; manufactured by Kyowa Medex Co., Ltd.). As a result, the concentration was 4,000 U per mL of the human blood.

Example 2 Affinity Purification of SCC-3 Cell-Derived sIL-2R

Purified IgG of an anti-sIL-2R rabbit polyclonal antibody prepared in our company was bound to CNBr-activated sepharose 4FF (GE Healthcare), and the antibody-bound resin was packed into a column. The culture supernatant recovered from the culture of the SCC-3 cells obtained in Example 1 was passed through the column, the column was washed with a sufficient amount of PBS, and a fraction containing sIL-2R was eluted with an elution buffer (0.1 M Citrate-Na containing 150 mM NaCl, pH 3.0). The fraction containing sIL-2R was concentrated with an ultrafiltration filter and then dialyzed against PBS to provide purified sIL-2R. The purified product was quantitatively determined by the same procedure as in Example 1 (CELL-FREE N IL-2R; manufactured by Kyowa Medex Co., Ltd.). As a result, it was found that 250,000 kU of the purified sIL-2R was obtained from 6 L of the culture supernatant.

Example 3 Generation of Monoclonal Antibody Using SCC-3 Cell-Derived sIL-2R as Immunogen (1) Generation of Anti-sIL-2R Antibody-Producing Hybridoma SCC-3 cell-derived sIL-2R purified in Example 2 was diluted with PBS and mixed with an equal amount of Freund's complete adjuvant to prepare an emulsion. The emulsion was subcutaneously injected into female BALB/c mice, C57BL/6JJcl mice, and F344/Jcl rats every week five times in an amount of 5 μg (corresponding to about 1,000 kU of sIL-2R)/dose per animal. Hybridomas were generated from antiserums obtained from each of the mice and rats by the same procedure as in Comparative Example 1 (1) to (4). A total of 8 kinds of hybridomas including 1 kind of BALB/c mouse-derived hybridoma (clone number; 92212), 1 kind of C57BL/6JJcl mouse-derived hybridoma (clone number; 92218), and 6 kinds of F344/Jcl rat-derived hybridomas (clone numbers; 92213R, 92214R, 92215R, 92216R, 92217R, and 92219R) were obtained. 92212 and 92215R out of the hybridomas were deposited by the applicant on Sep. 25, 2015 to NITE Patent Microorganisms Depositary (2-5-8 Kazusakamatari, Kisarazu, Chiba 292-0818, Japan).
92212: Receipt number: NITE BP-02124
92215R: Receipt number: NITE BP-02125

(2) Evaluation of Antibody Combination Applicable to Sandwich Immunoassay-1

A monoclonal anti-sIL-2R antibody was purified from each of the 8 kinds of hybridomas generated in the section (1), and a combination of antibodies enabling a sandwich ELISA system was evaluated by the same method as in Comparative Example 1 (5). The evaluation results of combinations of the 8 kinds of monoclonal antibodies are shown in Table 2. Absorbance changes at a level enabling the sandwich ELISA system were achieved in 33 combinations of the antibodies.

generated in Example 3, an antibody combination enabling the sandwich ELISA system was evaluated by the same method as in Comparative Example 1 (5). The results are shown in Table 3. Absorbance changes at a level enabling the sandwich ELISA system occurred in 122 combinations of the antibodies, but most thereof were combinations of the antibodies at least one of which was a monoclonal antibody using the SCC-3 cell-derived sIL-2R as an immunogen. Further, in the case of the combinations of the monoclonal antibodies using the SCC-3 cell-derived sIL-2R as an immu-

TABLE 2

| | | Immobilized antibody | | | | | | | |
|---|---|---|---|---|---|---|---|---|---|
| | | 92212 | 92213R | 92214R | 92215R | 92216R | 92217R | 92218 | 92219R |
| Biotin-labeled antibody | 92212 | | +++ | +++ | − | +++ | − | − | − |
| | 92213R | +++ | | − | +++ | − | +++ | ++ | +++ |
| | 92214R | +++ | − | | +++ | − | +++ | − | +++ |
| | 92215R | − | +++ | +++ | | +++ | − | − | +++ |
| | 92216R | +++ | − | − | +++ | | +++ | ++ | +++ |
| | 92217R | ++ | +++ | +++ | ++ | +++ | | − | +++ |
| | 92218 | − | +++ | +++ | − | +++ | − | | − |
| | 92219R | − | +++ | +++ | +++ | +++ | +++ | − | |

(3) Evaluation of Antibody Combination Applicable to Sandwich Immunoassay—2

For the total of 19 kinds of monoclonal anti-s IL-2R antibodies including the 11 kinds of antibodies generated in Comparative Example 1 and the 8 kinds of antibodies nogen, a large absorbance change occurred at a higher ratio. The results showed that the monoclonal anti-sIL-2R antibody generated by using the SCC-3 cell line-derived sIL-2R as an immunogen was suitable as an antibody for sandwich immunoassay.

TABLE 3

| | | Immobilized antibody | | | | | | | | | |
|---|---|---|---|---|---|---|---|---|---|---|---|
| | | 92201 | 92202 | 92203 | 92204R | 92205R | 92206R | 92207R | 92208R | 92209R | 92210R |
| Biotin-labeled antibody | 92201 | | − | − | − | − | − | − | − | − | − |
| | 92202 | − | | − | − | − | − | − | − | − | − |
| | 92203 | − | − | | − | − | − | − | − | − | − |
| | 92204R | − | − | − | | +++ | − | − | − | − | − |
| | 92205R | − | − | − | +++ | | − | − | − | − | − |
| | 92206R | − | − | − | − | − | | − | − | − | − |
| | 92207R | − | − | − | − | − | − | | − | − | − |
| | 92208R | − | − | − | − | − | − | − | | − | − |
| | 92209R | − | − | − | − | − | − | − | − | | − |
| | 92210R | − | − | − | − | − | − | − | − | − | |
| | 92211R | − | − | − | − | − | − | − | − | − | − |
| | 92212 | +++ | − | ++ | +++ | − | +++ | +++ | +++ | +++ | +++ |
| | 92213R | − | − | − | − | +++ | − | − | − | − | − |
| | 92214R | − | − | − | − | +++ | − | − | − | − | − |
| | 92215R | +++ | − | +++ | +++ | − | +++ | +++ | +++ | +++ | +++ |
| | 92216R | − | − | − | − | +++ | − | − | − | − | − |
| | 92217R | +++ | − | ++ | +++ | − | +++ | +++ | +++ | +++ | +++ |
| | 92218 | +++ | − | − | +++ | − | +++ | − | − | +++ | − |
| | 92219R | +++ | − | +++ | +++ | +++ | +++ | +++ | +++ | +++ | +++ |

| | | Immobilized antibody | | | | | | | | |
|---|---|---|---|---|---|---|---|---|---|
| | | 92211R | 92212 | 92213R | 92214R | 92215R | 92216R | 92217R | 92218 | 92219R |
| Biotin-labeled antibody | 92201 | − | +++ | − | − | +++ | − | +++ | − | +++ |
| | 92202 | − | +++ | − | − | +++ | − | +++ | − | ++ |
| | 92203 | − | +++ | − | − | +++ | − | +++ | − | +++ |
| | 92204R | − | +++ | − | − | +++ | − | +++ | ++ | +++ |
| | 92205R | − | − | +++ | +++ | ++ | +++ | ++ | − | +++ |
| | 92206R | − | +++ | − | − | +++ | − | +++ | − | +++ |
| | 92207R | − | +++ | − | − | +++ | − | +++ | − | +++ |
| | 92208R | − | +++ | − | − | +++ | − | +++ | − | +++ |
| | 92209R | − | +++ | − | − | +++ | − | − | − | − |
| | 92210R | − | +++ | − | − | +++ | − | +++ | − | +++ |
| | 92211R | | +++ | − | − | +++ | − | ++ | − | ++ |
| | 92212 | +++ | | +++ | +++ | − | +++ | − | − | − |

TABLE 3-continued

| | | | | | | | | |
|---|---|---|---|---|---|---|---|---|
| 92213R | − | +++ | | − | +++ | − | +++ | ++ | +++ |
| 92214R | − | +++ | − | | +++ | − | +++ | − | +++ |
| 92215R | +++ | − | +++ | +++ | | +++ | − | − | +++ |
| 92216R | − | +++ | − | − | +++ | | +++ | ++ | +++ |
| 92217R | +++ | ++ | +++ | +++ | ++ | +++ | | − | +++ |
| 92218 | +++ | − | +++ | +++ | − | +++ | − | | − |
| 92219R | +++ | − | +++ | +++ | +++ | +++ | +++ | − | |

Example 4 Structural Comparison Between SCC-3 Cell-Derived sIL-2R and Recombinant sIL-2R The results of the antibody combination evaluation of Example 3 suggested that there was a structural difference between a recombinants IL-2R protein and an SCC-3 cell-derived sIL-2R protein, and hence both the proteins were analyzed and their structures were compared to each other.

The SCC-3 cell line-derived purified sIL-2R (sample A) prepared in Example 2, the recombinant sIL-2R [Code: 200-02R] manufactured by peprotech (sample B) used in Comparative Example 1, and recombinant sIL-2R manufactured by R&D systems (sample C) were subjected to boiling treatment under an SDS-containing non-reducing condition. The treatment liquids were applied to lanes of SDS-PAGE (4% to 20%) at about 10 ng per lane to be subjected to electrophoresis. After the completion of the electrophoresis, the proteins were transferred from the gel to a PVDF membrane, subjected to a reaction with Biotylated Anti-human IL-2 Rα Goat Antibody (manufactured by R&D systems) at room temperature for 1 hour, and then subjected to a reaction with HRP-labeled streptavidin (manufactured by PIERCE) at room temperature for 30 minutes. After that, the IL-2R proteins were detected with 3,3'-diaminobenzidine and hydrogen peroxide. As a result, it was found that the SCC-3 cell-derived sIL-2R (A) and the recombinant sIL-2R manufactured by R/D systems (C) had the same molecular weight of around 30 kDa, whereas the recombinant sIL-2R manufactured by Peprotech (B) had a molecular weight of around 40 kDa, which was slightly large (FIG. 1).

Further, the SCC-3 cell-derived sIL-2R, the recombinant sIL-2Rs (rIL-2Rs; manufactured by Peprotech and manufactured by R/D systems), human PBMC-derived sIL-2R, and human serum containing highly concentrated sIL-2R were subjected to gel filtration chromatography analysis. 2,000 U of each sample was subjected to separation by gel filtration chromatography (column: HiLoad 16/60 Superdex 200 [GE Healthcare], eluent: PBS, flow rate: 1 mL/min), 2 mL of the elution fraction was fractionated, and the presence of the sIL-2R in each fraction was detected by sandwich ELISA. As a result, the elution position of the SCC-3 cell-derived sIL-2R coincided with those of the sIL-2R in human serum and the human PBMC-derived sIL-2R, whereas each of the two kinds of recombinant sIL-2Rs was eluted more slowly (FIG. 2). Accordingly, it was found that the SCC-3 cell-derived sIL-2R was estimated to have a structure similar to that of native human sIL-2R, whereas the recombinant sIL-2Rs were different in molecular weight from the native human sIL-2R under a non-denatured state.

The analysis results revealed that the recombinant sIL-2R proteins were different in structure from the sIL-2R protein present in human serum. It is estimated that this difference in structure may lead to the limited antigen specificities of the recombinant proteins, with the result that only the antibodies unsuitable for sandwich immunoassay were able to be generated. In contrast, the SCC-3 cell-derived sIL-2R has a structure similar to that of the sIL-2R present in human serum, and is considered to be more effective as an immunogen for anti-human sIL-2R antibody generation.

Example 5 Quantitative Determination of sIL-2R by LTIA Method

The antibody combination using the antibodies investigated in Example 3 (3) was investigated for its suitability as an antibody for latex turbidimetric immunoassay (LTIA). In the following Example, a concentration by % means (w/v) % unless otherwise stated.

(1) Preparation of Antibody-Supported Latex Particles
(a. Materials)
Anti-sIL-2R monoclonal antibody (92204R antibody) liquid: 0.5 Abs/mL (280 nm), sensitizing liquid: 20 mM MOPS-NaOH (pH 7.0)
Anti-sIL-2R monoclonal antibody (92212 antibody) liquid: 0.5 Abs/mL (280 nm), sensitizing liquid: 10 mM glycine-NaOH (pH 9.0)
Latex particles: average particle diameters 0.307 μm and 0.216 μm
(b. Method)
The 92204R antibody liquid and a 1% latex particle liquid (average particle diameter: 0.307 μm) diluted with the sensitizing liquid were mixed at an equal volume, and the mixture was stirred at 4° C. for 2 hours. After that, blocking was performed at 4° C. for 1 hour by adding an equal volume of 1% BSA to the mixed liquid. The resultant was dialyzed against MOPS buffer (pH 7.0). The resultant liquid was used as an antibody-supported latex particle solution.

Similarly, an antibody-supported latex particle solution using the 92212 antibody liquid and a 1% latex particle liquid (average particle diameter: 0.216 μm) diluted with the sensitizing liquid was obtained by the same method as described above.

(2) Preparation of LTIA Method First Reagent
A 30 mM Citrate-NaOH buffer (pH 6.0) containing 400 mM sodium chloride, 0.1% BSA, and 0.05% ProClin 300 was prepared and used as a first reagent.

(3) Preparation of LTIA Method Second Reagent
The 92212 antibody-supported latex particle solution and the 92204R antibody-supported latex particle solution were mixed with each other so that a content ratio between the latex particles was 1:1. The mixture was diluted with 5 mM MOPS buffer (pH 7.0) so as to have a final absorbance of 3.0 OD (600 nm) and used as a second reagent.

(4) LTIA Measurement
Human serum specimens (n=43) each of which had been measured for its sIL-2R concentration with a commercially available kit (CELL-FREE N IL-2R; manufactured by Kyowa Medex Co., Ltd.) in advance were prepared. The sIL-2R concentrations of those specimens were measured by an LTIA method using the first reagent and the second reagent. An automatic analyzer model 7170 manufactured by Hitachi, Ltd. was used for the measurement. Specifically, 100 μL of the first reagent was added to 4 μL of the human serum specimen, and the mixture was warmed at 37° C. for 5 minutes. After that, 100 μL of the second reagent was added, and the mixture was stirred. After that, absorbance changes (photometric point: 19 to 34) due to aggregate formation in 5 minutes were determined by measuring absorbances at a main wavelength of 570 nm and a sub wavelength of 800 nm.

The measurement results by the LTIA method showed a high correlation (r=0.922) with the measurement results with the commercially available kit (FIG. 3). Accordingly, it was found that the antibody generated by the SCC-3 cell-derived sIL-2R as an immunogen was suitable as an antibody for sandwich immunoassay, and was also applicable to the LTIA method. As described above, the SCC-3 cell-derived sIL-2R to be provided by the present invention and a method of producing an antibody using the SCC-3 cell-derived sIL-2R as an immunogen contribute to the construction of a reagent for human sIL-2R immunoassay.

The invention claimed is:

1. An anti-soluble interleukin-2 receptor antibody producing-hybridoma which is selected from the group consisting of 92212 (NITE BP-02124) and 92215R (NITE BP-02125).

2. An anti-soluble interleukin-2 receptor antibody, which is obtained by culturing the hybridoma of claim 1.

3. A reagent for measuring human soluble interleukin-2 receptor, comprising an anti-soluble interleukin-2 receptor antibody of claim 2.

4. The reagent according to claim 3, wherein the reagent comprises a reagent for performing latex turbidimetric immunoassay or sandwich ELISA.

* * * * *